United States Patent [19]

Dinka

[11] 4,436,816

[45] Mar. 13, 1984

[54] CELL GROWTH PROMOTING MATERIAL

[75] Inventor: Stephen K. Dinka, Washington Crossing, Pa.

[73] Assignee: Pitman-Moore, Inc., Washington Crossing, N.J.

[21] Appl. No.: 342,026

[22] Filed: Jan. 22, 1982

[51] Int. Cl.$^3$ .................. C12N 5/00; C12N 1/38; A61K 35/14

[52] U.S. Cl. .................. 435/240; 424/101; 435/244; 435/948

[58] Field of Search .............. 435/240, 241, 244, 948, 435/1, 2; 424/101; 426/657

[56] References Cited

U.S. PATENT DOCUMENTS

| | | | |
|---|---|---|---|
| 3,083,194 | 3/1963 | Thies et al. | 426/657 |
| 3,429,876 | 2/1969 | Bozicevich | 435/240 |
| 3,855,197 | 12/1974 | Hirsch et al. | 424/92 |
| 4,189,535 | 2/1980 | Dinka | 435/2 |

OTHER PUBLICATIONS

Heldin et al., "Partial Purification and Characterization of Platlet Factor Stimulating the Multiplication of Normal Human Cells", *Experiemntal Cell Research* 109, (1977), pp. 429-437.

Stiles et al., "Dual Control of Cell Growth By Somatomedins and Platlet Derived Growth Factor", *Proceedings of the National Academy of Sciences,* 76(3), (1979), pp. 1279-1283.

Shepard, "Somatomedin and Platlet Derived Growth Factors in Atheroschlerosis", *New England Journal of Medicine,* 303(11), (1980), pp. 641-642.

Hawley, "The Condensed Chemical Dictionary", 8th ed., (1971), p. 668.

Pavlu, "Fractionation of Proteins from Perchloric Acid Filtrates of Human Sera and of its Ethanol Fractions", *Acta Universitatis Carolinae Medica,* vol. 13 (5/6), (1967), pp. 417-422.

Uthne, "Human Somatomedins Purification and Some Studies on their Biological Actions", *Acta Endocrinologica* 73, (1973) pp. 1-35.

Rinderknecht et al., "Polypeptides with Nonsuppressible Insulin-Like and Cell Growth Promoting Activiteis in Human Serum", *Proceedings of the National Academy of Sciences,* 73(7), pp. 2365-2369, (1976).

Burgi et al., "Non-Suppressible Insulin Like Activity of Human Serum I: Physiochemical Properties Extraction and Purification", *Biochemica et Biophysica Acta* 121 (1966), pp. 349-359.

Ross et al., "Platlet Derrived Growth Factor", Cell 14 (1978), pp. 203-210.

Winzier et al., "Studies on the Mucoproteins of Human Plasma I: /Determination and Isolation", *Journal of Clinical Investigation* 27 (1948), pp. 609-616.

Groelke et al., "Serum Can Initiate DNA Synthesis in Cells Rendered Unresponsive to Insulin and Somatomedin", *Nature* 263 (9/76), pp. 140-142.

Zapf et al., "Binding of Nonsuppressible Insulinlike Activity to Human Serum", *Archives of Biochemistry and Biophysics* 168 (1975), pp. 638-645.

Philips et al., "Somatomedins", *New England Journal of Medicine* 302(7), (1980), pp. 371-380.

Ginsberg et al., "Identification and High Yield Purification of Insulin-like Growth Factors (NSILA and Somatomedins)". *Journal of Clinical Endocrinology and Metabolism,* 48(1), (1979), pp. 43-49.

Holley, "Serum Factors and Growth Control", *Cold Spring Harbor Conferences on Cell Proliferation,* vol. I (1974), pp. 13-18.

Ross et al., "Platlet-Derived Growth Factor and Plasma Control Cell Proliferation", *Cold Spring Harbor Conferences on Cell Proliferation* 6 (1979), pp. 3-16.

Gospaoarowicz et al., "Growth Factors in Mammalian Cell Culture", *Annual Review of Biochemistry,* 45 (1976), pp. 531-558.

Barnes et al., "Serum-Free Cell Culture: A Unifying Approach", Cell 22, (1980), pp. 649-655.

*Primary Examiner*—Esther M. Kepplinger
*Assistant Examiner*—John E. Tarcza

[57] ABSTRACT

Novel compositions for use as cell growth-promoting materials are made by the following novel process involving the steps of:

(a) slowly contacting serum or plasma with sufficient chilled perchloric acid to reach a 0.1 to 0.25 final molar concentration of said perchloric acid in said serum or plasma, (b) at a temperature of −1° C. to 15° C.,
(c) under intensive mixing which is continued until a homogeneous suspension is obtained,
(d) separating the resultant precipitate, which contains the growth-promoting substances, from the supernatant,
(e) eluting said growth-promoting substances from said precipitate by first resuspending said precipitate in an aqueous alkaline or salt solution, and thereafter,
(f) adjusting the pH to solubilize the growth-promoting substances from the insoluble proteins,
(g) separating the supernatant, which contains the growth-promoting substances, from the insoluble, undesired precipitate,
(h) exchanging the solvent in the supernatant for a physiological solution, and
(i) sterilizing the resultant growth-promoting material.

7 Claims, 1 Drawing Figure

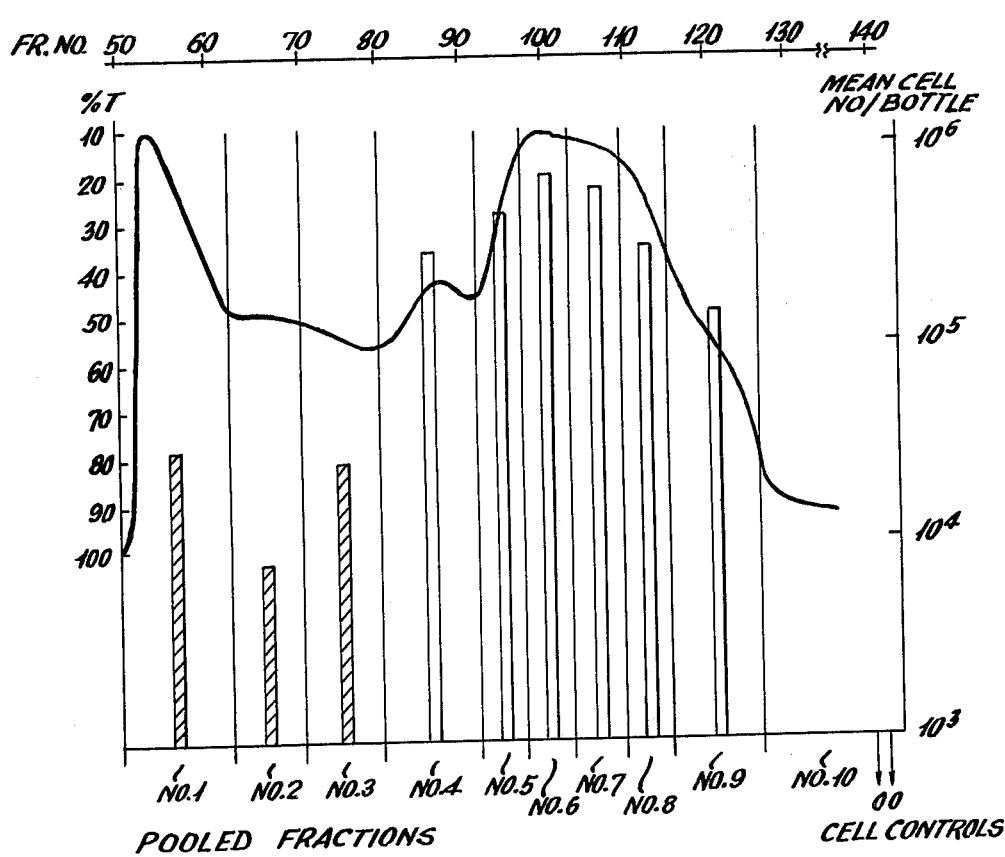

CELL GROWTH PROMOTING MATERIAL

FIELD OF THE INVENTION

This invention relates to cell growth promoting materials present in blood and in particular to compositions of and methods for the preparation of such materials.

BACKGROUND OF THE INVENTION

In order to understand cell growth of both normal and abnormal cells, scientists have sought to grow cells in chemically defined culture media. Cells grown in culture media are used for many different purposes and nearly all animal cells in culture require serum for growth. Serum is, however, a complex material containing many substances. Substances present in blood that promote cell growth (cell mitosis) have been termed "growth factors" (mitogens).

Some growth factors affect specific cells while other growth factors cause growth of a broader spectrum of cell types. Numerous scientists have sought means to isolate and purify substances responsible for cell growth. Some substances have been chemically identified and are polypeptide or protein in nature. Purification of such growth factors, usually present in very low concentration in blood, is extremely difficult. Techniques presently available for extraction of growth factors from these complex systems generally are not appropriate for processing large volumes of serum (D. Gospodarowica and J. S. Moran, in Ann. Rev. Biochem., 45, pp. 531-588, 1976). Methodologies available for the fractionation of proteinaceous growth factors from serum were reviewed in my earlier patent, U.S. Pat. No. 4,189,535. This patent teaches adsorption of serum proteins to anionic exchange resins followed by specific elution of growth promotant materials utilizing gradient salt or pH solutions.

One group of growth factors in blood are the somatomedins, a group of circulating peptides, believed to be of liver origin, that appear to be regulated by growth hormone. Somatomedins have been dissociated from larger carrier proteins in acidic environments and it has been shown that active somatomedin molecules of less than 10,000 dalton molecular weight are present in soluble form in ultrafiltrates of human plasma after acidification (pH 2.3) with acetic acid (B. H. Ginsberg et al., J. Clin. Endocrinology and Metabolism 48(1), 43-49, 1979). Although somatomedins can be recovered from plasma protein precipitates formed during Cohn fractionation they are dissociated from the carrier proteins by further acidification. The greater acid solubility of the dissociated somatomedins have been utilized in several methodologies for the collection of these growth promoters from Cohn-precipitated plasma protein. (H. Burgi et al, Biochem, Biophys. Acta. 121, 349-359, 1966; Knut Uthne, Acta Endocrinology (Suppl.) 175, 1-35, 1973; E. Rinderknecht and R. E. Humble, Proc. Natl. Acad. Sci. U.S.A., 73(7), 2365-2369, 1976).

During the blood coagulation process growth factors are released from blood platelets and some researchers have claimed a major portion of serum growth promoters are of platelet origin (R. Ross and A. Vogel, Cell, 14, 203-210, 1978). As a result of the fact that growth factors account for only a small percentage of all serum protein, investigators have isolated platelet growth factors from preparations of lysed washed platelets utilizing ion exchange chromatographic procedures. C. H. Heldin et al., (Exp. Cell Res. 109, 429-437, 1977) described two anionic fractions of 40,000 and less than 10,000 dalton molecular weight, respectively, and a heterogenous cationic fraction of from 25,000 to 35,000 dalton size possessing activity. Ross, et al (in Hormones and Cell Culture, Book A. Eds. G. H. Sato and R. Ross, pp 3-16 (Cold Spring Harbor Laboratory), 1979) isolated a cationic fraction of 10,000 to 30,000 molecular weight. Further processing resolved mitogenic activity to molecules of 16,000 to 18,000 daltons.

Several groups of investigators agree blood contains more than a single growth factor. For this reason, it appears desirable to develop a practical method of separating the diverse group of molecules possessing mitogenic activity from other blood proteins. In addition, there are not only many areas of practical application in which there may be made beneficial substitution of purified growth materials for whole serum or plasma, but the availability of growth material would make possible new areas of application of cell growth regulation. Some of the areas in which the availability of purified growth materials would be highly advantageous include the study of neoplastic diseases, dwarfism, neurological development, cellular immunity, transplantation (tissue grafting), wound healing and replacement of serum for virus vaccine production, for the production of biomolecules (e.g., urokinase, interferon, monoclonal antibodies, etc.), in animal husbandry for increasing and maintaining rapid growth and wherever serum or plasma is required for cell mitosis.

Thus, a purified growth material preparation would be desirable for many applications. The present invention results from a search for an economical procedure suitable for the isolation and purification of the low concentrations of growth promoters that are present in serum or plasma. Such a method will permit processing of moderate to large volumes of starting materials and will produce growth promoters in an active state, free of many of the non-growth promoting substances present in whole serum or plasma.

SUMMARY OF THE INVENTION

This invention relates to compositions comprising materials suitable for cell growth obtained from serum or plasma as well as a process for obtaining same. Said process is a two-step procedure involving specific acid precipitation and elution as more fully set forth hereinafter.

DETAILED DESCRIPTION OF THE INVENTION

According to the present invention there has been discovered a process for obtaining growth promoting material from serum or plasma which is simple and economically feasible, and further there has been obtained a growth promoting preparation having qualities not obtained in the literature described processes. The novel composition comprising growth promoting material may be prepared from serum or plasma employing a simple, substantially two-step operation: specific acid precipitation and elution.

The "growth promoting material" of the present invention may be one or more growth factors, i.e., chemical entities promoting cell mitosis. It may be a combination of materials which act together to promote cell growth. The growth promoting material has been found to be useful for promoting the growth of different cell types and appears to have broad growth promoting activity. Moreover, it has been found that the growth promoting material of the present invention may be obtained from serum or plasma without significant loss in activity.

The cell growth promoting material can be prepared by (1) adding perchloric acid (HClO$_4$, 70%) to serum or plasma to obtain a precipitate, and (2) extraction of the growth factors from the precipitate utilizing an aqueous solution with the pH of the suspension being increased, preferably to the physiologic range.

The serum or plasma useful as the starting material in the process may be obtained in a conventional manner from whole blood, usually mammalian blood. Conveniently, particularly for ultimate production on a large scale, bovine serum which is obtainable commercially may be employed. Alternatively, other sources of mammalian serum or plasma including ovine, porcine, human, canine, feline and others may be obtained by known procedures. The serum or plasma which is to be utilized may be stored, preferably in the frozen state, prior to use.

In carrying out the first step of the process to obtain an optimal yield, prechilled perchloric acid (70%) is added very slowly to the serum or plasma with intensive mixing. Foaming of the mixture should be avoided because of the potential of denaturation of the proteins. The preferred final concentration of the perchloric acid should be about 0.1 to 0.25 molar. After the perchloric acid addition, the mixing is continued for an additional period of time, e.g. 15 to 30 minutes in order to obtain the desired homogeneous suspension. The precipitate is then collected by normal means such as centrifugation or filtration.

In the second step of the process the elution is achieved by the addition of a prechilled aqueous solution to the precipitate. This addition is preferably carried out by the addition of small volumes of a prechilled aqueous solution to form a homogeneous paste. Whereas, most aqueous solutions are useful in the process, alkaline or salt solutions are preferred. This addition results in the solubilization of the growth promoters and permits their separation from the insoluble proteins by conventional means. The resulting solution containing the growth promoters is adjusted to physiological conditions to facilitate its utility. Known procedures to achieve the desired physiological conditions include dialysis, or other salt exchange processes. The resulting material is then sterilized using known procedures such as filtration, cobalt irradiation or the like.

The above process should be carried out at temperatures preferably from about −1° C. to 15° C. to avoid the denaturation of proteins and the growth of contaminants. The above procedure can be repeated if a growth factor preparation of greater purity is desired.

A preferred process for producing a composition comprising material suitable for promoting cell growth is as follows:

(1) adding slowly prechilled perchloric acid (HClO$_4$, 70%) to chilled serum or plasma under intensive mixing,
(2) continue mixing for a short period of time, e.g. 15 to 30 minutes,
(3) separating the resulting precipitate from the supernatant,
(4) eluting the precipitate by adding a prechilled aqueous solution (e.g. 0.2 molar sodium hydroxide) and resuspending the precipitate, preferably to form a fine slurry,
(5) adjusting the pH, preferably to pH 7.0–7.6,
(6) separating the supernatant from the insoluble precipitate,
(7) exchanging the solvent in the supernatant for a physiological solution, using dialysis or another known exchange procedure, and
(8) sterilizing the preparation using a known procedure.

The compositions comprising cell growth promoting substances prepared as described above, retain the essential cell growth promoting activity of native serum or plasma and are adapted to be employed in promoting growth of various cells.

Demonstrations of effectiveness of the compositions in promoting cell growth may be shown by the hereinafter described cell culture experiments in which the compositions of this invention or fetal calf serum was added to cell suspensions in nutrient culture medium and the effect on cell growth was determined. Representative test cell systems include human diploid skin fibroblast (SK 133) and lung fibroblast (MRC-5) cells, bovine (MDBK), canine (MDCK) and feline (CRFK) kidney cells. Representative nutrient culture medium suitable for carrying out the tests are those referred to as Eagle's minimum essential medium (originally described by Eagle, H. in Science, 130: 432 (1950) or modified with Earle's salts (Natl. Cancer Inst., 4:167 (1943) and available commercially (e.g. Grand Island Biological Company, Grand Island, NY or K. C. Biological, Inc., Lexena, Kansas). Commercially obtained Eagle's medium modified with Earle's salts to which had been added non-essential amino acids and sodium pyruvate were used for MRC-5, MDBK, MDCK and CRFK cells; for SK 133 cells commercially obtained Ham's Nutrient Mixture F-12 (Ham, R. G., Proc. N.A.S., U.S., 53:288–293, 1965) was used. These media supplemented with neomycin sulfate, polymixin B sulfate and amphotericin B (fungizone) were employed as the basic nutrient culture media in the hereinafter described representative experiments.

In the tests, the samples were separately added to appropriate cell suspensions in nutrient medium. The compositions of the present invention and the fetal calf serum were diluted with appropriate buffer solution in amounts to provide varying concentrations. The growth rate of cell cultures in the absence of growth factor or serum was determined by addition of an appropriate volume of buffer to the nutrient medium. The cell suspensions were prepared in volumes large enough to seed four bottles each. The cell cultures were incubated at 37° C. in 5 percent carbon dioxide atmosphere at saturated humidity. After an appropriate time of incubation, the cells were removed from the bottles by trypsin-EDTA. The cells from the corresponding bottles were counted.

The cell growth promoting substances of the present invention were found to promote growth of normal looking cells and to retain the essential activity present in the original serum.

Specific embodiments of the present invention are illustrated by the following representative examples. It will be understood, however, that the invention is not confined to the specific limitations set forth in the individual examples, but rather to the scope of the appended claims.

EXAMPLE I

To 5.0 liters of commercial adult bovine serum (stored frozen), mixed at 0° to +4° C. intensively, 90.0 milliliters of 70% perchloric acid was added very slowly. The mixing was continued for about fifteen minutes. The slurry was centrifuged and the supernatant discarded. To the precipitate 2,920 ml of 0.2 molar sodium hydroxide was added and a homogeneous suspension was prepared. The pH was adjusted to pH 7.4. The suspension was centrifuged. The supernatant was dialyzed exhaustively against 0.85% NaCl, pH 7.3 at +4° C. To 3,150 ml of the dialyzed supernatant under intensive mixing at 0° to +4° C., 45 ml of cold 70% perchloric acid was added very slowly. The mixing was continued for about fifteen minutes. The slurry was centrifuged and the supernatant discarded. To the precipitate 1,650 ml of 0.2 M. sodium hydroxide was added and a homogeneous suspension was prepared. The pH was adjusted to pH 7.5. The suspension was centrifuged and the supernatant was dialyzed against 0.85% NaCl, pH 7.3 at +4° C. The dialyzed supernatant representing the Bovine Serum Growth Factor Preparation (B.S.G.F.) was sterile filtered. Concentrations of B.S.G.F. ranging from 1 to 10% (v/v) in tissue culture medium were shown to support growth of various cell types. This is shown in Table I below:

TABLE 1

| | CELLS | | | | | | | |
|---|---|---|---|---|---|---|---|---|
| | MRC-5 | | MDBK | | MDCK | | CRFK | |
| | Cell Number per Bottle | | | | | | | |
| Test Sample | Mean$^a$ | SD | Mean$^b$ | SD | Mean$^b$ | SD | Mean$^b$ | SD |
| 1% v/v BSGF | 0.8 | 0.22 | 1.95 | 0.30 | 0.53 | 0.11 | 0.53 | 0.06 |
| 2% | 1.2 | 0.17 | 3.38 | 0.35 | 1.04 | 2.20 | 0.77 | 0.09 |
| 5% | 2.6 | 0.43 | 5.35 | 0.49 | 2.74 | 0.28 | 1.16 | 0.20 |
| 10% | 4.1 | 0.54 | 5.11 | 0.15 | 3.30 | 0.31 | 1.3 | 0.17 |
| 1% Fetal Bovine Serum | 1.2 | 0.42 | 1.28 | 0.24 | 1.10 | 0.20 | 0.62 | 0.11 |
| 2% | 3.4 | 0.56 | 2.84 | 0.39 | 1.03 | 0.22 | 0.87 | 0.10 |
| 5% | 3.9 | 0.46 | 3.91 | 0.29 | 2.26 | 0.35 | 0.90 | 0.17 |
| 10 | 6.2 | 0.53 | 4.35 | 0.32 | 1.74 | 0.29 | 1.46 | 0.28 |
| Cell Control | 0 | 0 | 0.01 | 0.01 | 0 | 0 | 0.04 | 0.02 |

$^a = \times 10^5$
$^b = \times 10^6$

The above clearly illustrates successful propagation of both human origin (MRC-5) and animal origin (MDBK, MDCK and CRFK) cells using the B.S.G.F.

EXAMPLE II

To 5,225 ml of commercial adult bovine serum (stored frozen) mixed at 0° to +4° C. intensively, 105 ml of 70% perchloric acid was added very slowly. The mixing was continued for about 30 minutes. The slurry was centrifuged and the supernatant discarded. To the precipitate 2,000 ml of 0.2 molar sodium hydroxide was added and a homogeneous suspension was prepared. The pH was adjusted to pH 7.4 and 500 ml of 0.85% NaCl, pH 7.4 was added. The suspension was centrifuged. The supernatant was dialyzed exhaustively against 0.85% NaCl, pH 7.4 at +4° C. The dialyzed supernatant representing the Bovine Serum Growth Factor Preparation (B.S.G.F.) was sterile filtered. Concentrations of B.S.G.F. ranging from 2 to 15% (v/v) in tissue culture medium were shown to support the growth of the highly fastidious SK 133 (diploid human skin fibroblast) cell line; a 1% B.S.G.F. (lowest concentration tested) supported the growth of Madin Darby Canine Kidney (MDCK) cells. These results are shown in Table 2 below:

TABLE 2

| | CELLS | | | |
|---|---|---|---|---|
| | MDCK | | SK 133 | |
| | Cell Number per Bottle | | | |
| Test Sample | Mean$^a$ | SD | Mean$^b$ | SD |
| 1% (v/v) BSGF | 0.66 | 0.06 | 0 | 0 |
| 2% | 0.70 | 0.05 | 0.19 | 0.08 |
| 5% | 0.88 | 0.14 | 0.83 | 0.11 |
| 10% | 0.97 | 0.08 | 0.90 | 0.18 |
| 15% | 1.47 | 0.24 | 1.30 | 0.36 |
| 1% Fetal Bovine Serum | 0.30 | 0.05 | 0.68 | 0.18 |
| 2% | 0.58 | 0.06 | 1.10 | 0.21 |
| 5% | 1.85 | 0.13 | 1.50 | 0.17 |
| 10% | 1.94 | 0.14 | 1.90 | 0.34 |
| Cell Control | 0.03 | 0.18 | 0 | 0 |

$^a = \times 10^6$
$^b = \times 10^5$

EXAMPLE III

To 5,410 ml of commercial adult bovine serum (stored frozen), mixed at 0° to 4° C. intensively, 97.5 ml of cold 70% perchloric acid was added very slowly. The mixing was continued for 30 minutes. The slurry was centrifuged, and the supernatant discarded. To the precipitate 2,700 ml of 0.2 molar sodium hydroxide was added and a homogenous suspension was prepared. The pH was adjusted to pH 7.3. The suspension was centrifuged. The supernatant was dialyzed exhaustively against 0.85% NaCl, pH 7.3 at +4° C. The dialyzed supernatant representing the B.S.G.F. was sterile filtered. The B.S.F.G. was tested using MDBK culture. The results, as shown in Table 3, demonstrate the activity of this preparation. Growth promotant activity was observed when B.S.G.F. in concentrations ranging from 1 to 5% (v/v) was added to tissue culture medium and used to culture MDBK cells. Cell yields were higher than from cultures treated with similar concentrations of fetal bovine serum. A 10% (v/v) concentration of B.S.G.F. supported growth of SK 133 cells, although cell yield was lower than when an equivalent concentration of fetal bovine serum was used.

TABLE 3

| | CELL NUMBER PER BOTTLE | |
|---|---|---|
| TEST SAMPLE | MEAN | SD |
| WITH MDBK CELLS | | |
| 1% (v/v) B.S.G.F. | 2.23 × 10$^6$ | 0.27 × 10$^6$ |
| 2% | 3.44 × 10$^6$ | 0.27 × 10$^6$ |

TABLE 3-continued

| TEST SAMPLE | CELL NUMBER PER BOTTLE | |
|---|---|---|
| | MEAN | SD |
| 5% | $4.26 \times 10^6$ | $0.60 \times 10^6$ |
| 10% B.S.G.F. Pooled Sephacryl Fraction No. | | |
| 10% 1 | 0 | |
| 10% 2 | 0 | |
| 10% 3 | 0 | |
| 10% 4 | $0.29 \times 10^6$ | $0.12 \times 10^6$ |
| 10% 5 | $0.45 \times 10^6$ | $0.12 \times 10^6$ |
| 10% 6 | $0.70 \times 10^6$ | $0.18 \times 10^6$ |
| 10% 7 | $0.60 \times 10^6$ | $0.19 \times 10^6$ |
| 10% 8 | $0.31 \times 10^6$ | $0.12 \times 10^6$ |
| 10% 9 | $0.14 \times 10^6$ | $0.09 \times 10^6$ |
| 10% 10 | 0 | |
| 1% Fetal Bovine Serum | $1.39 \times 10^6$ | $0.22 \times 10^6$ |
| 2% | $1.95 \times 10^6$ | $0.23 \times 10^6$ |
| 5% | $3.59 \times 10^6$ | $0.50 \times 10^6$ |
| Cell Control | 0 | |
| WITH SK 133 CELLS | | |
| 10% (v/v) B.S.G.F. | $0.68 \times 10^5$ | $0.18 \times 10^5$ |
| 10% B.S.G.F. Pooled Sephacryl Fraction No. | $0.30 \times 10^5$ | $0.17 \times 10^5$ |
| 1 | $0.30 \times 10^5$ | $0.17 \times 10^5$ |
| 2 | $0.08 \times 10^5$ | $0.11 \times 10^5$ |
| 3 | $0.26 \times 10^5$ | $0.16 \times 10^5$ |
| 4 | Very Few Cells | |
| 5 | " | |
| 6 | " | |
| 7 | " | |
| 8 | " | |
| 9 | " | |
| 10 | " | |
| 10% Fetal Bovine Serum | $2.1 \times 10^5$ | $0.34 \times 10^5$ |
| Cell Control | 0 | |

Gel filtration was employed to estimate the size and relative quantitative distribution of growth promotant substances present in a B.S.G.F. preparation. For this method a 5 cm diameter×87 cm high Sephacryl S-300 Superfine column (Pharmacia Fine Chemicals Co.) was prepared and equilibrated with phosphate buffered saline pH 7.4 at +4° C. The calibration proteins employed were thyroglobulin (M.W. 669,000), ferritin (M.W. 440,000), aldolase (M.W. 158,000), bovine albumin (M.W. 67,000), ovalbumin (M.W. 43,000), chymotrypsinogen A. (M.W. 25,000) and ribonuclease A (M.W. 13,700).

In separate operations, 50 ml samples of B.S.G.F. preparation of Example III and samples of the calibration proteins were applied, and chromatographed with phosphate buffered saline, pH 7.4 at +4° C. at a flow rate of 105 ml per hour. 10.5 ml fractions were collected. The fractions, as represented by the graph in FIG. 1, were pooled and sterilized. The pooled fractions were tested for cell growth promoting activity using SK 133 and MDBK cells. For MDBK cells the growth promotent activity was present in pooled fractions No. 4 through 9 of the material collected after Sephacryl S-300 chromatography, representing molecules of diverse molecular weight (approx. 10,000 to 300,000 daltons). For SK 133 cells the activity was detected in pooled chromatographic fractions No. 1 through 3 representing molecules of approximately 200,000 daltons, or greater molecular weight. These data indicate the presence of different cell type specific activities in the preparation.

In addition to the preferred embodiments described herein, other embodiments, arrangements and variations within the spirit of the invention and the scope of the appended claims will occur to those skilled in the art.

I claim:

1. A process for preparing growth promoting material, whose effectiveness can be demonstrated by in vitro cell culture experiments, which comprises:
   (a) slowly contacting serum or plasma with sufficient chilled perchloric acid to reach a 0.1 to 0.25 final molar concentration of said perchloric acid in said serum or plasma,
   (b) at a temperature of −1° C. to 15° C.,
   (c) under intensive mixing which is continued until a homogeneous suspension is obtained,
   (d) separating the resultant precipitate, which contains the growth-promoting substances, from the supernatant,
   (e) eluting said growth-promoting substances from said precipitate by first resuspending said precipitate in an aqueous alkaline or salt solution, and thereafter,
   (f) adjusting the pH to solubilize the growth-promoting substances from the insoluble proteins,
   (g) separating the supernatant, which contains the growth-promoting substances, from the insoluble, undesired precipitate,
   (h) exchanging the solvent in the supernatant for a physiological solution, and
   (i) sterilizing the resultant growth-promoting material.

2. The process of claim 1 wherein serum is utilized in step (a).

3. The process of claim 2 wherein the serum is bovine serum.

4. The process of claim 1 wherein plasma is utilized in step (a).

5. A composition comprising material suitable for promoting cell growth, whose effectiveness can be demonstrated by in vitro cell culture experiments in both human and animal-derived cell types at a level comparable to the activity of Fetal Bovine Serum, said material prepared by a process which comprises:
   (a) slowly contacting serum or plasma, derived from non-fetal bovine blood, with sufficient chilled perchloric acid to reach a 0.1 to 0.25 final molar concentration of said perchloric acid in said serum or plasma,
   (b) at a temperature of −1° C. to 15° C.,
   (c) under intensive mixing which is continued until a homogeneous suspension is obtained,
   (d) separating the resultant precipitate, which contains the growth-promoting substances, from the supernatant,
   (e) eluting said growth-promoting substances from said precipitate by first resuspending said precipitate in an aqueous alkaline or salt solution, and thereafter,
   (f) adjusting the pH to solubilize the growth-promoting substances from the insoluble proteins,
   (g) separating the supernatant, which contains the growth-promoting substances, from the insoluble, undesired precipitate,
   (h) exchanging the solvent in the supernatant for a physiological solution, and
   (i) sterilizing the resultant growth-promoting material.

6. The composition of claim 5 wherein serum is utilized in step (a).

7. The composition of claim 5 wherein plasma is utilized in step (a).

* * * * *